United States Patent [19]

Lodzinski

[11] 4,222,064
[45] Sep. 9, 1980

[54] OPTICAL PROPERTY MEASUREMENT SYSTEM AND METHOD

[75] Inventor: Fred P. Lodzinski, Port Edwards, Wis.

[73] Assignee: Nekoosa Papers Inc., Port Edwards, Wis.

[21] Appl. No.: 775,631

[22] Filed: Mar. 7, 1977

Related U.S. Application Data

[60] Division of Ser. No. 543,902, Jan. 24, 1975, and a continuation-in-part of Ser. No. 429,637, Dec. 28, 1973, abandoned, and Ser. No. 540,251, Jan. 10, 1975, Pat. No. 4,019,819.

[51] Int. Cl.$^2$ ............................................. G01N 21/00
[52] U.S. Cl. ....................................... 356/73; 356/429
[58] Field of Search .................. 356/199, 200, 73, 429

[56] References Cited

U.S. PATENT DOCUMENTS

| | | | |
|---|---|---|---|
| 2,429,331 | 10/1947 | Sachtleben | 356/430 |
| 3,827,808 | 8/1974 | Cho | 356/199 |

FOREIGN PATENT DOCUMENTS

| | | |
|---|---|---|
| 1164527 | 9/1969 | United Kingdom . |
| 323718 | 2/1972 | U.S.S.R. ................................. 356/200 |

OTHER PUBLICATIONS

Rutledge; "Extended outputs from a system with an On-Line Tristimulus Colorimeter & a Digital Computer", Tappi, vol. 54, No. 7, Jul. 71, pp. 1152-1155.

Primary Examiner—Vincent P. McGraw
Attorney, Agent, or Firm—Hill, Van Santen, Steadman, Chiara & Simpson

[57] ABSTRACT

In an illustrated embodiment, brightness, color, opacity and fluorescent contribution to brightness are measured by an on-line sensing head providing for simultaneous measurement of transmitted and reflected light. By measuring two independent optical parameters, paper optical properties of a partially translucent web are accurately characterized substantially independently of paper grade and weight. The instrument is designed so as to be capable of transverse scanning of a moving paper web on the paper machine, and so as to monitor desired paper optical characteristics with sufficient accuracy to enable on-line control of the optical characteristics of the paper being manufactured. Advantageously, several sets of reflectance and transmittance values based on respective common spectral response functions are sensed continuously and/or simultaneously during movement of the web.

24 Claims, 4 Drawing Figures

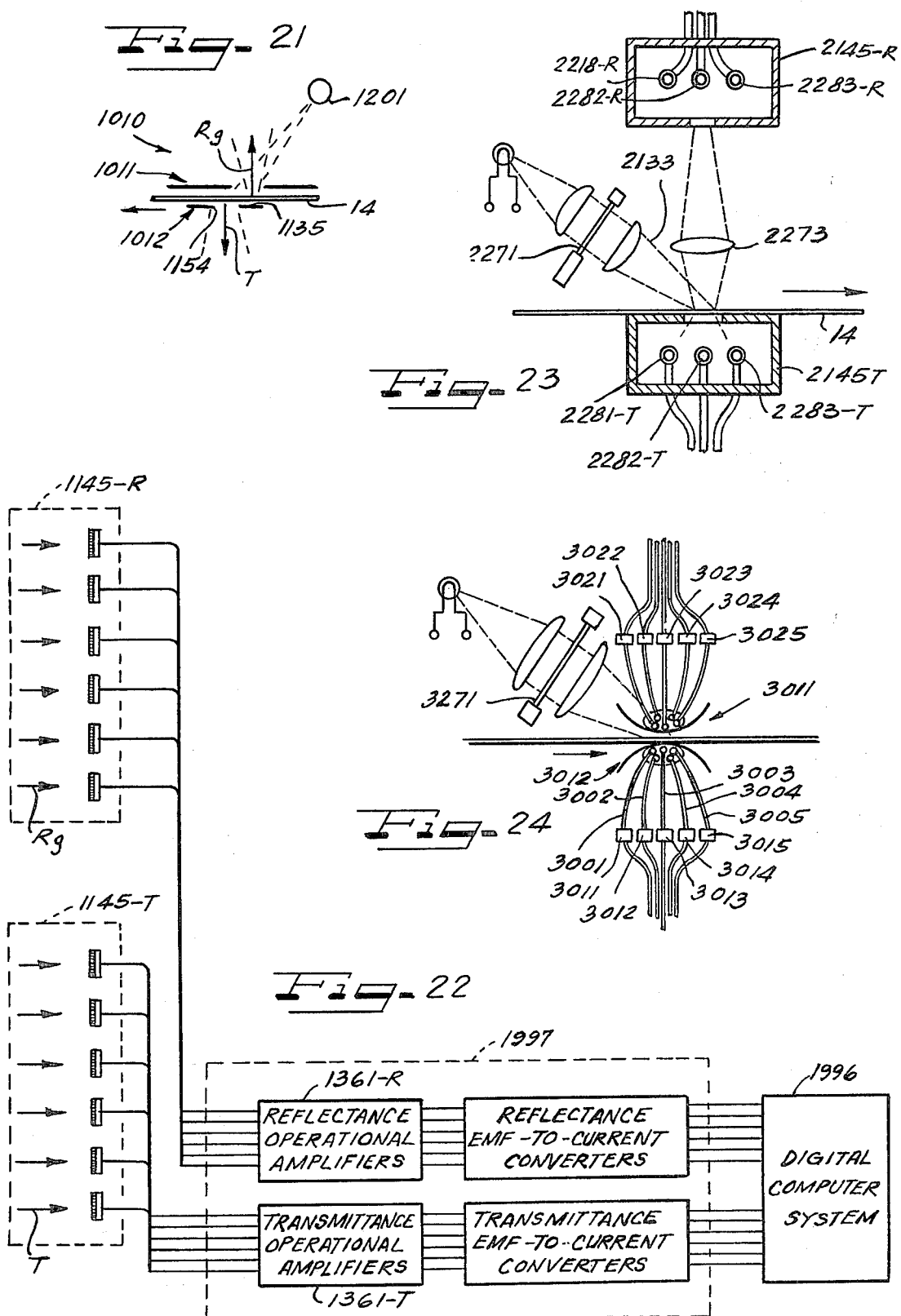

OPTICAL PROPERTY MEASUREMENT SYSTEM AND METHOD

CROSS-REFERENCE TO RELATED APPLICATIONS

This is a division of application Ser. No. 543,902, filed Jan. 24, 1975.

The present application is a continuation-in-part of my copending application Ser. No. 429,637 filed Dec. 28, 1973, abandoned, and of my copending application Ser. No. 540,251 filed Jan. 10, 1975, and the written disclosure and drawings of each of these copending applications are incorporated herein by reference in their entireties. Said application Ser. No. 540,251 issued as U.S. Pat. No. 4,019,819 on Apr. 26, 1977.

BACKGROUND OF THE INVENTION

In the prior art it is known to obtain an indication of color and brightness characteristics of a paper web during manufacture by an on-line measurement of reflectance value (Rg), but this measurement is decidedly different from that necessary for actual color and brightness characterizations. Accordingly, such a measurement must be accompanied by very frequent off-line testing, so as to enable an adequate empirical calibration of the measuring instrument. Further, a separate set of calibration parameters is required for each grade and weight of paper. Off-line instruments which adequately measure these characteristics require that a pad of several thicknesses of paper be exposed to the light source aperture so that a different reflectance value (Roo) is obtained. Obviously this is impossible with an on-line instrument unless the far more inaccessible reel itself is tested.

Only where the on-line measured reflectance value (Rg) approaches the off-line value (Roo), as in instances of paper of extremely high opacity such as heavily coated or heavily dyed paper, can the above problems be minimized to the point where accuracy becomes sufficient for control purposes.

There is some possibility that the prior art includes the sequential measurement of two separate reflectance parameters such as one with a backing of near zero absolute reflectance and one with a white backing, but there appears to be no concept of a multiple property measurement system and method utilizing corresponding multiple sets of parameter measurements based on respective common spectral response functions and the prior art concept may be largely limited to a direct determination of Tappi opacity and/or to an abstract investigation of the feasibility of determining absolute reflectance (Roo) at a given wavelength such as 457 nanometers.

SUMMARY OF THE INVENTION

This invention relates to an optical device and method for sensing optical properties of a substantially homogeneous sheet material, and particularly to an on-the-paper-machine device and method for simultaneously sensing both transmitted and reflected light so as to obtain measurements from which the optical properties of interest can be calculated substantially independently of grade and weight of paper involved.

Accordingly it is an object of the present invention to provide an optical monitoring device and method for sensing optical properties based on measurements made on a single thickness of partially translucent substantially homogeneous sheet material and which measurements sufficiently characterize the actual properties of interest that a minimum of empirical calibration is required regardless of changes in grade and weight of paper.

Another object of the invention is to provide such an optical monitoring device and method capable of accurately sensing two or more optical properties such as brightness, color, opacity and/or fluorescent contribution to brightness preferably essentially continuously, or at least substantially simultaneously, and especially adapted for operation with a continuously moving web.

With such an optical monitoring device is useful off-line for sensing optical properties of a single thickness sample, it is a further important object of the present invention to provide such an optical monitoring device which is of sufficiently light weight and compact construction so as to be adapted for on-line monitoring of the desired optical properties.

Another and further object of the invention is to provide an on-the-paper-machine optical monitoring device of sufficient flexability and accuracy to enable control of desired optical properties during the paper making process.

A unique feature of the on-line optical monitoring device is its ability to essentially simultaneously measure both reflected and transmitted light. By measuring two independent optical parameters it is possible to thoroughly characterize the paper optical properties of a partially translucent web with a minimum of empirical correction for factors such as paper grade and weight. Preferably a plurality of sets of optical parameters are sensed continuously or at least substantially simultaneously.

Other objects, features and advantages of the present invention will become apparent from the following detailed description taken in connection with the accompanying drawings.

INCORPORATION BY REFERENCE

For a disclosure of a complete optical property measurement system relating to the present invention, reference is made to FIGS. one through twenty and the description thereof of U.S. Pat. No. 4,019,819 issued Apr. 26, 1977.

BRIEF DESCRIPTION OF THE DRAWINGS

FIGS. 1 through 20 are briefly described in U.S. Pat. No. 4,019,819 referenced above, at column 2, line 20 through line 64.

FIG. 21 is a diagrammatic view illustrating the embodiment described in the section entitled "Proposed Instrument Design" of the aforementioned copending applications;

FIG. 22 illustrates further details of the embodiment of FIG. 21 as described in the copending applications;

FIG. 23 shows an embodiment similar to that of FIGS. 21 and 22, but with the interior of the transmittance cavity providing the backing for the reflectance measurements; and FIG. 24 shows an embodiment similar to that of FIGS. 21 and 22, but utilizing multiple sets of reflectance and transmittance optical light pipes.

DESCRIPTION OF THE PREFERRED EMBODIMENTS

DESCRIPTION OF FIGS. 21 AND 22

An instrument 1010 is shown in FIG. 21 made up of two scanning sensing heads 1011 and 1012, one above and one below the moving paper web 14, and a dedicated computer with appropriate couplers for input and output forms part of digital computer system 1996, FIG. 22. The bottom head 1012 receives light transmitted through the sheet and subsequently analyzed for its X, Y, and Z tristimulus components. It also contains a backing 1135 of some specified effective reflectance (for example a black body of zero, or near zero, reflectance) located just ahead or behind (machine direction) relative to entrance 1154 of the transmitted light receptor compartment indicated at 1145-T, FIG. 22.

The upper head 1011 contains light source means 1201 as well as a reflected light receptor indicated at 1145-R, FIG. 22. The latter receives light energy after reflection from the moving web at a point just above the backing 1135, on the bottom head 1012 and the reflected light energy would also be analyzed for its X, Y, and Z tristimulus components. Both light receivers 1145-R and 1145-T and, for that matter, the light source means 1201 itself may be integrating cavities of a type. This would be one way to insure the uniform distribution of emitted, transmitted, and reflected light in the X-direction in addition to providing identical samples of light going to each photoelectric cell installed with filters within the cavities themselves, this arrangement being represented in FIG. 22. The flux of the light source means 1201 could be monitored or controlled by a third partial, or full, set of filter-photocell combinations. The availability of both the transmitted (T) and reflected ($R_g$) light signals described above and as indicated in FIGS. 21 and 22 allows for precise computation of the reflectance with an infinite backing ($R_{oo}$). It is the latter, $R_{oo}$ value, which is required to characterize color, brightness, and an index of fluorescence. In addition, it would eliminate the need for any grade corrections in measuring either printing or TAPPI opacity, both of which could be made available if desired.

A small, rather low-cost, dedicated computer such as that forming part of system 1996 with appropriate interface equipment such as indicated at 1997 could be used to receive all signals, compute all pertinent optical properties, and determine the signal for direct, closed loop control of:

a. 2-5 separate conventional dye additions;
 b. fluorescent dye feed to the size press; and
 c. PKT, $TiO_2$, or other slurry flow;

so that brightness, opacity, color (L, a,b) and fluorescence could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads 1011 and 1012 to optical measurements and flow feeds with which paper manufacturers are familiar. The combined mathematical technology above is also sufficient for adequate decoupling of this otherwise complicated information so that overlapped control is avoided.

Use of dedicated computer would eliminate most of the electronics now associated with optical measuring equipment. It could also be used to integrate results across the web and simplify and/or maintain calibration. The package would lend itself to rather universal application and minimize the time and effort on the part of the purchaser.

The key feature of the instrument 1010 which distinguishes it from existing on-line optical testers, is that it provides for the measurement of both transmitted and reflected light without undue complications. This, in turn, can cause a great deal of improvements regarding sensitivity, accuracy, flexibility, and thoroughness of a continuous optical property measuring device.

DESCRIPTION OF FIGS. 23 and 24

FIGS. 23 and 24 show further means by which the incorporated patent applications can be employed without the use of a mechanically operated filter wheel.

In FIG. 23, an ultra violet light absorbing filter is located at 2271, and the U.V. filtered incident light beam 2133 is directed to impinge upon the moving web 14.

Transmitted light is collected within the integrating cavity 2145-T below the web, just as in the embodiment of FIGS. 1-6. The resulting intensity and color of this light is analyzed in a manner comparable to such embodiment by employing, for example, six separate ports containing six different filter-photocell combinations including filters such as 2281-T, 2282-T and 2283-T (and as shown in FIG. 22) representing Brightness, $X_R$, $X_B$, Z, $Y_C$, and $Y_A$, respectively. The output of each photocell could be read continuously or intermittently by means of a computer equipped with appropriate interface electronics as in the previous embodiments.

The reflected light component is directed through an appropriate lens system 2273 into a second integrating cavity 2145-R located above the moving web. Its intensity and color is, likewise, analyzed by the use of six filter-photocell combinations including filters such as 2281-R, 2282-R and 2283-R (and as shown in FIG. 22) and connected eventually to the same computer.

FIG. 24 is similar to FIG. 23 except that fiber optics (light conveying tubes) are utilized in place of the integrating cavities. A representative portion of the transmitted light is directed into each of six such tubes (five of the tubes being indicated at 3001-3005 in FIG. 24) which are ended by means of specific spectral response filters (Br, $X_R$, $X_B$, Z, $Y_C$, $Y_A$,) and corresponding photocells, five of the filter-photocell combinations being indicated at 3011-3015. The same is done for the reflected light by means of filter-photocell combinations five being indicated at 3021-3025. All twelve outputs of this example are again read either continuously or intermittently by a computer.

The fluorescent component of light resulting from the use of "optical brightners" is not included in any of the above measurements. It can be measured, of course, by mechanically removing the U.V. incident beam filter and synchronizing such change with a status change to the computer. A short time later the U.V. filter is reinstated back into position. A rotating U.V. filter-chopper could be employed at 3271 providing proper synchronization of the computer data storage is also accomplished.

The set of twelve fiber optic light paths as shown in FIG. 24 may define six simultaneously operative reflectance light paths in upper sensing head 3011 and six simultaneously operative transmittance light paths in lower sensing head 3012. The six reflectance fiber optic paths include respective filters corresponding to filters 281-286 and respective individual photocells located to receive respective portions of the reflected light which is reflected generally along a path such as that indicated at 137 in FIG. 3. The six transmittance fiber optic paths would also include respective filters corresponding to filters 281-286 and respective individual photocells located to receive respective portions of the transmitted light which is transmitted generally along paths corresponding to paths 141-143 in FIG. 3. The filter means in the incident light path includes a filter 3271 similar to filters 271 and 272 for filtering out the ultraviolet component from the incident beam, so that the twelve simultaneous photocell readings corresponding to those designated RSD1 through RSD6, and TSD1 through TSD6 (when the device is off-sheet), and corresponding to those designated RSP1 through RSP6, and TSP1 through TSP6 (when the device is on-sheet), will exclude a fluorescent contribution. (See Table 3 where this notation is introduced in U.S. Pat. No. 4,019,819.)

If a reflectance reading corresponding to RSD7 (when the device is off-sheet) and corresponding to RSP7 (when the device is on-sheet) is desired so as to enable computation of fluorescent contribution to brightness, it is necessary to mechanically remove the ultraviolet filter 3271 from the incident light path, or otherwise introduce an ultraviolet component of proper magnitude, and obtain another brightness (Z), reading, for example from the number four reflectance photocell.

As an alternative to the above filter optic system with a common incident light path as shown in FIG. 24, seven fiber optical tubes incorporating filters corresponding to 281-287 of FIGS. 3 and 4, respectively, at say the light exit points of the tubes, could be used to supply the incident light to seven different points on the paper web. The reflected light from each of these seven points could be monitored by seven different systems, each involving lenses and a phtocell such as shown in FIG. 24, and the number seven reflected light path including also a filter corresponding to filter 288, FIG. 4. The transmitted light from the first six points would also need to be kept separately, and this could be accomplished by six integrating cavities and six photocells.

As a further alternative the seven fiber optical tubes defining the seven incident light paths could have a second set of seven filter optical tubes and photocells respectively disposed to receive reflected light from the respective illuminated points as in FIG. 24. Another set of six fiber optical tubes and photocells could be associated with the first six illuminated points for receiving transmitted light as in FIG. 24. This could eliminate the need for the light collecting lenses in the upper sensing head and the integrating cavities in the lower sensing head.

The last two mentioned alternatives with seven fiber optical tubes defining the incident light paths appear to be rather complicated systems, but they do offer means of eliminating both the mechanical filter wheel as well as any mechanical device to control the presence of ultraviolet light in the incident beam.

Still another alternative is to use "screens" in addition to the filters in the embodiments of FIGS. 21-24. The new photodiodes are considered sensitive enough to measure reduced light intensities so that screens with different transmittance values could be used with six of the incident beam filters or with the reflectance and transmittance filters so that the net photocell output for each reflectance light path, and for each transmittance light path, would be similar enough so that separate and individual pre-amplification for the respective reflectance outputs would not be necessary, and so that separate and individual preamplification for each transmittance output would not be necessary. This means that the feedback paths for the twelve amplifiers of components 1361-R and 1361-T in FIG. 22, for example, could have the same resistance values.

The term "screen" is understood in the art as referring to a network of completely opaque regions and intervening openings or completely translucent regions, such that light energy is uniformly attenuated over the entire spectrum by an amount dependent on the proportion of opaque to transmitting area.

I claim as my invention:

1. In the art of paper manufacture, apparatus for obtaining a quantitative measure of a plurality of paper optical properties, which comprises:
    (a) an on-machine optical monitoring device for mounting on a paper machine and having a web receiving region for receiving in operative relation thereto a moving web of paper sheet material being produced by such machine,
    (b) said on-machine optical monitoring device having an optical system with at least two sets of substantially independent photometric sensor means and at least two sets of partly distinct light energy paths each light energy path of each set including at least light source means and a respective spectral response filter means and a respective one of said sets of photometric sensor means and each light energy path of each set intersecting said web receiving region prior to the respective associated photometric sensor means,
    (c) said at least two sets of partly distinct light energy paths comprising respective reflectance light energy paths and respective transmittance light energy paths having respective common spectral response characteristics of substantial bandwidths and of responses over such bandwidths for essentially simulating respective predetermined paper optical property measurement spectral functions such as to characterize said paper optical properties, and
    (d) the respective photometric sensor means of each set being arranged on respective opposite sides of the web receiving region for collecting respectively reflected and transmitted light energy from a web of paper sheet material at said web receiving region and said sets of photometric sensor means providing respective sets of reflectance and transmittance output signals essentially characterizing respective sets of two essentially independent optical response parameters of the paper sheet material based on the respective predetermined paper optical property measurement spectral functions and such as to characterize said paper optical properties with substantially greater accuracy than any characterization of said paper optical properties by either one of such optical response parameters of the respective sets taken by itself.

2. The apparatus of claim 1, further comprising automatically operating digital computer means connected on line with said on-machine optical monitoring device and coupled with the respective sets of photometric sensor means for automatically storing respective individual signals of respective sets of reflectance and transmittance signals in accordance with the respective sets of reflectance and transmittance output signals from the sets of said photometric sensor means for automatically calculating said paper optical properties on the basis of non-linear relationships between such paper optical properties and the reflectance and transmittance values of said paper sheet material, thereby to provide quantitative measures from which at least two of paper brightness, paper color and paper opacity may be controlled during paper manufacture.

3. Apparatus according to claim 1 with one set of said two partly distinct light energy paths each having a common spectral response characteristic substantially corresponding to a standard brightness measurement spectral distribution of light energy.

4. Apparatus according to claim 1 with one set of said two partly distinct light energy paths each having a spectral response characteristic with an effective wavelength of substantially 457 nanometers and with a wavelength bandwidth and shape essentially in accordance with the standard brightness spectral distribution for characterizing TAPPI brightness.

5. Apparatus according to claim 1 with one set of said two light energy paths each having a spectral response characteristic essentially simulating the C.I.E. tristimulus $\bar{y}$ spectral response function.

6. Apparatus according to claim 2 with said automatically operating digital computer means including means for automatically computing TAPPI opacity.

7. Apparatus according to claim 2 with said automatically operating digital computer means including means for automatically computing printing opacity.

8. Apparatus according to claim 1 with said optical system providing at least three respective common spectral response characteristics for three respective sets of said two partly distinct light energy paths and said paths together providing three sets of reflectance and transmittance output signals for a given portion of said web such as to characterize the color of the portion of said web of paper sheet material with substantially greater accuracy than any characterization of said color of said paper sheet material by either one of the reflectance and transmittance output signals of the three sets taken alone.

9. Apparatus according to claim 8 with said reflectance and transmittance light energy paths having respectively in common spectral response characteristics for essentially simulating the C.I.E. tristimulus $\bar{x}$, $\bar{y}$ and $\bar{z}$ spectral functions.

10. Apparatus according to claim 1 with said optical system including said light source means, said filter means and said photometric sensor means providing respectively standard brightness, C.I.E. tristimulus $\bar{x}$, $\bar{y}$, $\bar{z}$, and standard opacity spectral response characteristics in common for respective sets of partly distinct light energy paths, said sets of photometric sensor means providing respective sets of reflectance and transmittance output signals for characterizing standard brightness, the color and opacity of the single thickness paper sheet material.

11. The method of sensing a plurality of optical properties which comprises:

(a) impinging a broad spectrum of visible light on a substantial area of one surface of a single thickness of substantially homogeneous sheet material by means of an optical measuring system, (b) optically viewing the illuminated area of said substantially homogeneous sheet material by means of respective sets of physically separate light energy paths of matched spectral response characteristics, (c) independently and substantially simultaneously photometrically sensing the light energy of the respective sets of physically separate light energy paths, and (d) filtering light energy transmitted along the respective sets of of light energy paths in accordance with respective matched pairs of spectral response characteristics simulating respective optical property measurement spectral response functions, and generating by means of said optical measuring system respective pairs of essentially distinct optical response parameters for characterizing the respective optical properties of said single thickness of substantially homogeneous sheet material more accurately than any characterization by either optical response parameter of the pairs taken alone, and without any need for physically changing of a backing for said sheet material.

12. Apparatus for controlling the production of paper sheet material including an optical measuring device having a receiving region for receiving in operative relation thereto a single thickness of paper sheet material, said optical measuring device having an optical system with at least four substantially independent photometric sensors and at least four at least partly distinct light energy paths each including at least light source and spectral response filter means and a respective one of said photometric sensors, and each intersecting said receiving region prior to the respective associated photometric sensor, said light source means supplying a spectrum of light energy to the light energy paths accommodating characterization of any one of a plurality of paper optical properties comprising at least two of color, brightness and opacity, said paths being respectively arranged for collecting reflected and transmitted light energy from the receiving region after impingement of the light energy on a single thickness of paper sheet material at said region to provide reflectance and transmittance measurements which essentially characterize a plurality of said paper optical properties.

13. Apparatus according to claim 12 wherein the reflectance and transmittance measurements characterize the color and opacity of the paper sheet material and means responsive to said measurements for controlling the addition of coloring dyes and opacifying pigment during manufacture of the paper sheet material.

14. Apparatus according to claim 12 wherein the photometric sensors supply substantially simultaneous reflectance and transmittance measurements which characterize the color and opacity of the paper sheet material.

15. Apparatus according to claim 12 wherein the reflectance and transmittance measurements characterize the color and brightness of the paper sheet material and are utilized to control the addition of coloring dyes and optical brightener during manufacture of the paper sheet material.

16. Apparatus according to claim 12 wherein the photometric sensors supply substantially simultaneous reflectance and transmittance measurements which characterize the color and brightness of the paper sheet material.

17. In the art of paper manufacture, apparatus for obtaining a quantitative measure of paper optical properties, which comprises an on-machine optical monitoring device for mounting on a paper machine in operative association with a moving web of paper sheet material being produced by such machine, and comprising a light source means for supplying light energy to a web of paper sheet material sufficient to characterize a plurality of paper optical properties including at least opacity and color, and light receptor means disposed for collecting light energy from said light source means after impingement on a web of paper sheet material and for photometrically sensing said light energy to generate respective output signals sufficient to characterize said plurality of paper optical properties including at least opacity and color, means comprising said light receptor means of said on-machine optical monitoring device defining at least four distinct light energy collecting paths and including respective substantially independent photometric sensors operatively associated with the respective paths, for collecting and responding to respective different spectral distributions of light energy after impingement on a web of paper sheet material, under respective sufficiently differentiated conditions so as to provide at least four substantially independent output signals which together are sufficient to essentially characterize opacity and color of the paper sheet material.

18. Apparatus according to claim 17 with said on-machine optical monitoring device having means connected with said substantially independent photometric sensors for responding to said output signals to supply respective quantitative indications of said plurality of paper optical properties including at least opacity and color.

19. Optical property measuring apparatus which comprises: a color and opacity sensing device having a material receiving region for receiving a single thickness of sheet material whose color and opacity is to be sensed, and comprising an optical assembly and a backing assembly for mounting at respective opposite sides of the material receiving region, said optical assembly having light source means, spectral response filter means and photometric sensor means providing a plurality of reflectance sensing light paths having respective spectral response characteristics such as together to define substantially a tristimulus spectral distribution, said reflectance sensing light paths extending from the light source means toward the backing assembly so as to impinge on the material receiving region for reflection from a sheet material in said region and backed by said backing assembly, and extending from the material receiving region to the photometric sensing means so as to provide respective reflectance output signals representing the respective reflectance values of the sheet material in said region in reference to the respective spectral response characteristics of the respective reflectance sensing light paths, said backing assembly together with said optical assembly further providing a transmittance sensing light path including photometric sensor means, and said transmittance sensing light path extending from the light source means toward and through said material receiving region, and said backing assembly having light transmitting aperture means communicating with the material receiving region, the transmittance sensing light path extending through said aperture means so that light energy is transmitted through sheet material at the material receiving region and through the aperture means of the backing assembly for photometric evaluation by the photometric sensing means, and the transmittance sensing light path thereby providing a transmittance output signal representing a transmittance value of sheet material in said region, and said sensing device characterizing the color and opacity of sheet material in said region by means of both said reflectance and said transmittance values.

20. Apparatus for obtaining a quantitative measure of optical properties of a moving web of substantially homogeneous sheet material, which comprises:
(a) an optical monitoring device having a web receiving region for receiving in operative relation thereto a web of sheet material moving along a web path,
(b) said optical monitoring device having an optical system with photometric sensor means capable of providing simultaneously at least four essentially independent output signals and with at least four partly distinct light energy paths each including common light source means, and spectral response filter means and said photometric sensor means, said photometric sensor means being responsive to light energy received from the web receiving region after impingement on sheet material in said region,
(c) said four partly distinct light energy paths being respectively arranged for collecting reflected and transmitted light energy from the web receiving region after reflection from and transmission through said web under respective substantially different conditions so as to provide the respective essentially independent output signals from said photometric sensor means such as to essentially characterize at least four essentially independent optical response parameters of the sheet material.

21. Apparatus for obtaining a quantitative measure of optical properties, which comprises an on-machine optical device for mounting in operative association with a moving web of sheet material, and comprising a light source means for supplying light energy to a web of sheet material sufficient to characterize a plurality of paper optical properties including at least color and opacity, and light receptor means disposed for collecting the light energy after impingement thereof on a web of paper sheet material, said light receptor means defining a plurality of reflectance and transmittance light energy collecting paths and including respective substantially independent photometric sensors operatively associated with the respective paths, for collecting respective different spectral distributions of said light energy to provide substantially independent output signals which together are sufficient to essentially characterize the color and opacity of the sheet material.

22. Apparatus according to claim 21 with said on-machine optical device having means connected with said substantially independent photometric sensors for responding to said output signals to supply respective qutntitative indications of said plurality of paper optical properties including at least color and opacity.

23. Apparatus according to claim 21 with said optical device having a material receiving region for receiving the web of sheet material whose color and opacity is to be sensed, and comprising an optical assembly and a backing assembly for mounting at respective opposite sides of the material receiving region, said optical assembly having a plurality of reflectance sensing light energy collecting paths having respective spectral response characteristics such as together to define substantially a tristimulus spectral distribution, said reflectance sensing light energy collecting paths extending from the light source means toward the backing assembly so as to impinge on the material receiving region for reflection from a web in said region and backed by said backing assembly, and extending from the material receiving region to respective separate photometric sensors so as to provide respective reflectance output signals representing the respective reflectance values of the sheet material in said region in reference to the respective spectral response characteristics of the respective reflectance sensing light paths, said backing assembly together with said optical assembly further providing a transmittance sensing light energy collecting path extending from the light source means toward and through said material receiving region, and said backing assembly having light transmitting aperture means communicating with the material receiving region, the transmittance sensing light energy collecting path extending through said aperture means so that light energy is transmitted through sheet material at the material receiving region and through the aperture means of the backing assembly for photometric evaluation by a photometric sensor of said backing asssembly.

24. Apparatus for obtaining a quantitative measure of a plurality of optical properties, which comprises an on-machine optical device having a sheet receiving region for receiving sheet material, and comprising a light source means for supplying a predetermined spectral distribution of light energy to a web of sheet material sufficient to characterize a plurality of paper optical properties, and light receptor means disposed for collecting the light energy after impingement thereof on a sheet material and for photometrically sensing respective different spectral distributions of said light energy to generate respective output signals sufficient to characterize said plurality of paper optical properties, said light receptor means comprising an optical assembly and a backing assembly for mounting at respective opposite sides of the sheet receiving region, said optical assembly having a plurality of photometric sensors and providing a plurality of reflectance sensing light paths having respective spectral response characteristics such as together to define a color measuring spectral distribution of light energy, said reflectance sensing light paths extending from the light source means toward the backing assembly so as to impinge on the sheet receiving region for reflection from a sheet material in said region and backed by said backing assembly, and extending from the material receiving region to the respective photometric sensors so as to provide respective reflectance output signals representing the respective reflectance values of the sheet material in said region in reference to the respective spectral response characteristics of the respective reflectance sensing light paths, said backing assembly having a photometric sensor therein and said backing assembly together with said optical assembly further providing a transmittance sensing light path including said photometric sensor in said backing assembly, and said transmittance sensing light path extending from the light source means toward and through said sheet receiving region, and said backing assembly having light transmitting aperture means communicating with the sheet receiving region, the transmittance sensing light path extending through said aperture means so that light energy is transmitted through sheet material at the sheet receiving region and through the aperture means of the backing assembly for photometric evaluation by the photometric sensor, and the photometric sensors of the optical assembly and backing assembly providing reflectance and transmittance output signals representing reflectance and transmittance values of sheet material in said region for characterizing said plurality of properties of said sheet material in said region.

* * * * *